(12) United States Patent
Egger et al.

(10) Patent No.: US 9,335,268 B2
(45) Date of Patent: May 10, 2016

(54) DEVICE AND METHOD FOR DETERMINING THE CONCENTRATION OF FLUOROPHORES IN A SAMPLE

(71) Applicant: LRE Medical GmbH, Münich (DE)

(72) Inventors: Rafael Egger, München (DE); Jörg Zeiner, München (DE)

(73) Assignee: LRE Medical GmbH, Munich (DE)

( * ) Notice: Subject to any disclaimer, the term of this patent is extended or adjusted under 35 U.S.C. 154(b) by 26 days.

(21) Appl. No.: 14/607,274

(22) Filed: Jan. 28, 2015

(65) Prior Publication Data

US 2015/0137008 A1    May 21, 2015

Related U.S. Application Data

(62) Division of application No. 13/444,027, filed on Apr. 11, 2012, now Pat. No. 9,006,685.

(30) Foreign Application Priority Data

Apr. 15, 2011   (DE) .......................... 10 2011 002 080

(51) Int. Cl.
   *G01N 21/64*   (2006.01)
   *G01N 21/27*   (2006.01)

(52) U.S. Cl.
   CPC ............ *G01N 21/645* (2013.01); *G01N 21/278* (2013.01); *G01N 2201/062* (2013.01); *G01N 2201/068* (2013.01); *G01N 2201/06113* (2013.01)

(58) Field of Classification Search
   CPC .................. G01N 2201/062; G01N 2201/068;
   G01N 2201/06113; G01N 21/645; G01N 21/278; G01N 21/274; G01N 21/276
   See application file for complete search history.

(56) References Cited

U.S. PATENT DOCUMENTS 6,242,114 B1   6/2001   Yamasaki et al.
6,471,916 B1   10/2002  Noblett
(Continued)

FOREIGN PATENT DOCUMENTS

AT           502194 A4    2/2007
DE          3212219 A1   11/1982
(Continued)

*Primary Examiner* — Yara B Green
(74) *Attorney, Agent, or Firm* — McCormick, Paulding & Huber LLP

(57) ABSTRACT

A device (10) and a method for analyzing a sample (16) containing fluorophores use a light source (12) emitting light ($\lambda_{ex}$) onto the sample (16), and onto a fluorescence standard (14). The fluorophores of the sample (16), given an immission of light of a first wavelength ($\lambda_{ex1}$), have a first excitation efficiency and, given an immission of light of a second wavelength ($\lambda_{ex2}$), have a second excitation efficiency. The fluorescence standard (14), given the same immissions of light, has a third excitation efficiency and, a fourth excitation efficiency. An optical element (20) which is arranged between the light source (12) and the sample (16) and/or (12) the fluorescence standard (14) adapts, due to its optical property, a first difference between the first excitation efficiency and the second excitation efficiency and a second difference between the third excitation efficiency and the fourth excitation efficiency to each other.

12 Claims, 9 Drawing Sheets

(56) References Cited

U.S. PATENT DOCUMENTS

| | | |
|---|---|---|
| 7,115,232 B2 | 10/2006 | Hudson |
| 2005/0251027 A1 | 11/2005 | Liu et al. |
| 2007/0121099 A1 | 5/2007 | Matsumoto et al. |
| 2010/0117003 A1 * | 5/2010 | Egger ................ G01N 21/6428 250/459.1 |
| 2011/0028806 A1 | 2/2011 | Merritt et al. |
| 2011/0085168 A1 | 4/2011 | Phillips et al. |

FOREIGN PATENT DOCUMENTS

| | | |
|---|---|---|
| DE | 4106042 A1 | 8/1991 |
| DE | 4026821 A1 | 3/1992 |
| DE | 19858206 A1 | 6/2000 |
| DE | 10200865 A1 | 10/2002 |
| DE | 102004044717 A1 | 3/2006 |
| DE | 102004047593 A1 | 4/2006 |
| DE | 102005032249 A1 | 1/2007 |
| DE | 102008027548 A1 | 12/2009 |
| DE | 102008033214 A1 | 1/2010 |
| EP | 0237363 A2 | 9/1987 |
| EP | 0478026 A1 | 4/1992 |
| EP | 1265529 A1 | 12/2002 |
| EP | 1635164 A2 | 3/2006 |
| GB | 2150704 A | 7/1985 |
| WO | 0172222 A1 | 10/2001 |
| WO | 2007068021 A1 | 6/2007 |

* cited by examiner

DEVICE AND METHOD FOR DETERMINING THE CONCENTRATION OF FLUOROPHORES IN A SAMPLE

CROSS REFERENCE TO RELATED APPLICATIONS

This application is a divisional of U.S. patent application Ser. No. 13/444,027, filed Apr. 11, 2012, which claims the priority of German patent application No. 10 2011 002 080.2, filed on Apr. 15, 2011, the disclosures of which are incorporated herein by reference.

FIELD OF THE INVENTION

The invention relates to a device for determining the concentration of fluorophores in a sample, the sample in particular comprising a substance marked with fluorophores. Further, the invention relates to a corresponding method.

BACKGROUND OF THE INVENTION

In known devices and methods for the quantitative determination of the concentration of fluorophores of at least one substance in a sample, the sample is irradiated with light of an excitation wavelength emitted from an excitation light source. The intensity of the fluorescent light of an emission wavelength emitted from the sample is measured by means of a detection element. Such a device and such a method are, for example, known from DE 10 2008 057 115 A1.

In order to guarantee exact measurement results, a reference object, in particular a so-called fluorescence standard or a suitable optical element, is used to calibrate a measured intensity value of the fluorescent light. When irradiated with excitation light of a predetermined wavelength and intensity, the reference object emits light having a known wavelength distribution and/or intensity. The long-term stability of fluorescence standards is often insufficient, whereas the use of an optical element as a reference object, as known from DE 10 2008 057 115 A1, guarantees the required long-term stability. Reference objects can be used as a calibration standard as well as additionally or alternatively as a quality assurance standard or as a reference standard for the direct referencing of performed measurements. Reference standards are often used in so-called scanning systems in which the reference standard and at least one sample are successively irradiated with light, and the light that is incident on a detection element and comes from the reference standard is detected as a first measurement value and the light that is incident on the detection element and comes from the sample is detected as a second measurement value, wherein by means of the ratio of the first measurement value to the second measurement value the concentration of fluorophores in the sample is determined. Preferably, the invention, too, can be realized as a scanning system.

From EP 0 237 363 A2, a method and a device for determining the fluorescence of a test sample are known. From U.S. Pat. No. 6,242,114 an optical composite having fluorescent properties is known, which comprises a support layer with fluorescent material, which is optically coupled to a selective spectral filter.

In the fluorescence-based analysis of samples, in particular of body fluids, for example in the fluorescence-based analysis of sample fluids applied to test strips, in known devices absolute values are determined by a referencing with an internal reference standard. The excitation efficiency of the fluorophore used for analyzing the sample is generally wavelength-dependent so that the sample or the test strip with the sample is irradiated with a narrow-band light having a preset intensity in order to be able to draw conclusions on the number of fluorophores and thus on the amount of a substance in the sample to which the fluorophores have been attached based on the light emitted from the sample or, respectively, the test strip. A change in the spectrum of the light source generating the excitation light, in particular a shift in the wavelength of the light emitted from the light source, partially results in considerable distortions of the measurement result, in particular a change in wavelength has a very different effect or has an even opposite effect on the light emitted from the fluorophores and on the light emitted from the reference object. The wavelength or, respectively, the wavelength spectrum of the light source can, for example, change due to temperature influences. Further, such a change in wavelength is also possible as a result of so-called spontaneous jumps which may occur in the course of the lifetime of the light source. Such spontaneous jumps, for example, occur in the case of lasers used as a light source. In the case of a change in wavelength as a result of temperature influences, a compensation can be accomplished with a suitable algorithm by way of a temperature measurement in that the temperature influences are appropriately taken into account in the evaluation of the measurement values. In the case of the mentioned spontaneous wavelength jumps, such a compensation is not possible so that there will be faulty measurements.

It is the object of the invention to specify devices and methods for determining the concentration of fluorophores in a sample, by which the influence on a measurement result due to a changing wavelength of the light source used for illuminating the sample is reduced.

SUMMARY OF THE INVENTION

This object is solved by a device and method having the features of the present invention. Advantageous aspects and developments of the invention are specified the following description.

By a device and method having the features of the present invention, it is achieved each time that the influence of a change in wavelength of the light source on a measurement result to be determined for analyzing the sample is reduced by the optical element or is completely compensated for by the optical element. For this, in accordance with the device in one form, the optical element can be arranged between the light source and the sample or between the light source and the reference object. Due to its optical property, the optical element results in that a first difference between a first excitation efficiency of the fluorophores of the sample given an emission of light of a first wavelength and a second excitation efficiency of the fluorophores of the sample given the emission of light of a second wavelength and a second difference between a first excitation efficiency of the fluorophores of the fluorescence standard given the emission of light of the first wavelength and a second excitation efficiency of the fluorophores of the fluorescence standard given an emission of light of the second wavelength onto the fluorescence standard are brought into approximate correspondence with each other. On the other hand, in the device according to claim 2 the light emitted from the excitation light source is emitted onto the sample and emitted onto a monitor diode that is provided for monitoring the intensity of the light radiation generated by the light source. By means of such a monitor diode, the intensity of the light radiation emitted from the light source can be kept constant via a control circuit, as this is described, for example, in DE 10 2008 057 115 A1.

In particular the ratio of the energy supplied to the sample or, respectively, the fluorophores by the immission of light to the energy used therefrom for the excitation of the fluorophores is referred to as excitation efficiency.

According to a further aspect of the invention, also a method can be provided in which by means of an excitation light source excitation light is emitted onto a substance of a sample containing fluorophores. Further, by means of the excitation light source excitation light is emitted onto a monitor diode. Given an emission of excitation light of a first wavelength the fluorophores of the sample have a first excitation efficiency and given an emission of excitation light of a second wavelength they have a second excitation efficiency. The fluorophores of the sample emit fluorescent light in the direction of the detection element in the case of an immission of excitation light. Further, a reference light source for emitting reference light onto the reference object and for emitting excitation light onto the monitor diode is provided. By the optical reference object a part of the reference light emitted from the reference light source is coupled in the direction of a detection element.

Given an emission of excitation light of a first wavelength, the monitor diode has a first detection sensitivity, and given the emission of excitation light of a second wavelength it has a second detection sensitivity. By means of an optical element arranged between the excitation light source and the sample and/or between the excitation light source and the monitor diode a first difference between the first excitation efficiency and the second excitation efficiency and a second difference between the first detection sensitivity and the second detection sensitivity are adapted to each other due to the optical property of the optical element. As a result thereof, the effects of the change in the detection sensitivity of the monitor diode given a change in wavelength as well as of a change in the excitation efficiency of the fluorophores given a change in wavelength can be reduced or completely compensated for at least in a wavelength range between the first wavelength and the second wavelength.

In a development of this further aspect of the invention, as well as in a development of the device using a detection element, at least a part of the fluorescent light of an emission wavelength that is emitted from the sample is incident on the detection element which detects a corresponding first measurement value. A part of the reference light that is coupled in is incident on the detection element which detects a corresponding second measurement value. The ratio of the first measurement value to the second measurement value is determined, and the number of fluorophores of the substance of the sample in a detection area is determined taking into account the determined ratio of first measurement value and second measurement value.

It is advantageous when, during a calibration of the device, the optical reference element couples in the constant part of the reference light emitted from the reference light source in the direction of the detection element and a third measurement value corresponding to the part of the light that is coupled in and that is incident on the detection element is detected, wherein a fluorescence standard is irradiated with the excitation light emitted from the excitation light source, and a fourth measurement value corresponding to the part of the fluorescent light emitted from the fluorescence standard that is incident on the detection element is detected. In this way, an easy calibration of the device by means of a fluorescence standard can be performed. Further, it is advantageous to use a reemission standard as an optical reference object.

The number of fluorophores in the sample can be determined according to the following formula:

$$FD_P = \frac{E_{mes2}}{E_{s2}} \cdot X$$

wherein $FD_P$ is the number of fluorophores of the sample, $E_{mes2}$ is a second measurement value corresponding to the part of the fluorescent light of an emission wavelength coming from the sample and being incident on the receiving element, $E_{s2}$ is a first measurement value corresponding to the part of the light that is coupled in and that is incident on the receiving element, and X is a constant scaling factor which represents a relation between the used optical element (REM) and the fluorescence standard and which is determined for the optical element (REM) during the calibration of the measuring device.

The scaling factor X can be determined according to the following equation:

$$X = \frac{E_{s1}}{E_{mes1}} \cdot FD_{FS}$$

wherein $E_{s1}$ is a third measurement value corresponding to the constant part of the reference light that is emitted from the reference light source and is incident on the receiving element, which constant part is coupled in by the optical element in the direction of the receiving element during the calibration, $E_{mes1}$ is a fourth measurement value corresponding to the part of the fluorescent light that is emitted from the fluorescence standard and is incident on the receiving element, and $FD_{FS}$ is the known number of fluorophores of the fluorescence standard in the detection area.

Preferably, the optical path between the reference light source and the optical reference object that serves to couple in the constant part of the reference light emitted from the reference light source in the direction of the detection element goes through the same optical elements as the optical path of the excitation light between the excitation light source and the sample or, respectively, the excitation light source and the fluorescence standard.

The following embodiments for an advantageous development of the invention are generally referred to a light source. These developments can then be advantageously used in connection with the light source in the various forms of the invention.

In general, the first wavelength and the second wavelength, the first excitation efficiency and second excitation efficiency, the third excitation efficiency and the fourth excitation efficiency, the first detection sensitivity and the second detection sensitivity differ from one another each time.

In an advantageous development of the invention, a detection element for detecting the light emitted from the sample given an emission of light of the light source onto the sample and/or for detecting the light emitted from the fluorescence standard given an emission of light of the light source onto the fluorescence standard can be provided. In this connection, the detection element can determine a feature value of a feature of the light emitted from the sample, such as the brightness or the intensity of the light radiation, given an emission of light of the light source onto the sample. Further, the detection element can determine a feature value of the same feature of the light emitted from the fluorescence standard given an emission of light of the light source onto the reference object.

Due to its optical property, the optical element which is arranged between the light source and the sample and/or between the light source and the reference object influences, in the case of a change in wavelength of the light emitted from the light source in at least one wavelength range, the light emitted onto the sample and/or the light emitted onto the fluorescence standard and/or the light emitted from the sample and/or the light emitted from the fluorescence standard such that the detection element determines a first feature value that is dependent on the light emitted from the sample and a second feature value that is dependent on the light emitted from the reference object, wherein the change in the difference between the first feature value and the second feature value over the wavelength range is reduced or the difference is completely removed by the optical element. In this way, it is achieved that a detection element determines measurement values or, respectively, detection values for analyzing the sample, in particular the intensity of the fluorescence light emitted from the fluorophores contained in the sample can be detected easily. For referencing this measurement or for calibrating the device or for quality assurance of the analysis performed by means of the device or, respectively, by means of the method, also the light emitted from the fluorescence standard can be detected by means of the detection element and a corresponding detection value or, respectively, measurement value can be determined. Further, it is advantageous when the detection element upon detection of the light emitted from the sample as a result of an immission of light of the light source onto the sample determines a detection value by means of which a control unit determines the quantity of the fluorophores in the sample and/or the concentration of a substance in the sample marked with the fluorophores. In this way, the fluorophore concentration and thus the amount of the substance in the sample marked by means of the fluorophores can be determined easily.

Further, it is advantageous when the optical property of the optical element influences the light emitted from the sample upon immission of light of the light source, the light emitted onto the sample, the light emitted onto the fluorescence standard, the light emitted onto the monitor diode and/or the light emitted from the fluorescence standard such that the first difference is approximated to the second difference, preferably that the second difference is equal to the first difference. In this way, the different excitation efficiencies and detection sensitivities can at least in part be compensated for by means of the optical element and thus in an easy manner.

Further, it is advantageous when the optical element adapts the spectral curve of the excitation efficiency of the fluorophores of the sample and the spectral curve of the excitation efficiency of the fluorophores of the fluorescence standard at least in the wavelength range between the first wavelength and the second wavelength. As a result thereof, also wavelength shifts in the wavelength range between the first wavelength and the second wavelength are completely or at least in part compensated for.

It is particularly advantageous when the first wavelength is the nominal wavelength of the light source and when the second wavelength is a wavelength different from the first wavelength, which in particular arises due to temperature influences and/or aging of at least one component of the light source and/or an optical element arranged in the beam path between light source and sample, between light source and monitor diode and/or between light source and reference object. According to the invention, such changes in the wavelength between the first and the second wavelength can be compensated for easily at least in part.

The difference between the first wavelength and the second wavelength can be in the range between 0.1 nm and 5 nm in the case of common light sources. As a result thereof, deviations of the wavelength or, respectively, of the wavelength spectrum of the light emitted from the light source can be compensated for, as they might occur in practice in the case of common light sources. As a light source in particular a laser light source, an LED light source or a white light source having a filter arrangement for generating light in a narrow-band range can be used. The first wavelength lies in the narrow-band range, preferably in the middle thereof. This narrow-band range is the nominal wavelength range provided for this light source. The second wavelength lies outside the middle of this nominal wavelength range, preferably outside the nominal wavelength range. As a result thereof, also a deviation of a nominal wavelength range to be generated by the light source arrangement can be handled by the invention at least such that no or only a little influence on the determined measurement results due to the change in wavelength is to be expected.

Preferably, the light source can emit light successively onto the sample and onto the fluorescence standard or, respectively, onto the sample and onto the reference object. This is in particular useful in devices in which the reference object or the fluorescence standard is not used as a reference standard but as a quality assurance standard or as a calibration standard, wherein then the reference object is inserted into the device or used in the method instead of a sample. As a result thereof, easy reference measurements between the sample and the reference object or, respectively, the fluorescence standard are possible so that exact analyses of samples can be performed. In particular, the fluorescence standard or, respectively, the reference object and at least one sample can be successively illuminated with light in scanning systems, each time the light that is incident on the detecting element being detected.

Alternatively, the light source can simultaneously emit light onto the sample and onto the reference object or onto the sample and the monitor diode or onto the sample, the reference object and the monitor diode. As a result thereof, no adjusting elements have to be provided to emit the light optionally onto the sample, the monitor diode or the reference object.

It is particularly advantageous when the optical element which is arranged between the light source and the sample and/or between the light source and the reference object or, respectively, between the light source and the fluorescence standard, is an optical filter, wherein the optical property of the optical element is then the transmission property of the filter. An optical filter can be produced easily with a desired optical property. As a result thereof, the optical property of a filter to be produced can be designed and produced dependent on the requirement resulting from the first difference and the second difference so that an easy long-time stable compensation of the effects of a change in wavelength of the light source onto the excitation sensitivity of the fluorophores, the detection sensitivity of a monitor diode and/or the emission sensitivity of the reference object is possible.

BRIEF DESCRIPTION OF THE DRAWINGS

Further features and advantages of the invention result from the following description which in connection with the enclosed Figures explains the invention in more detail with reference to embodiments.

DESCRIPTION OF THE PREFERRED EMBODIMENTS

Figure 1:
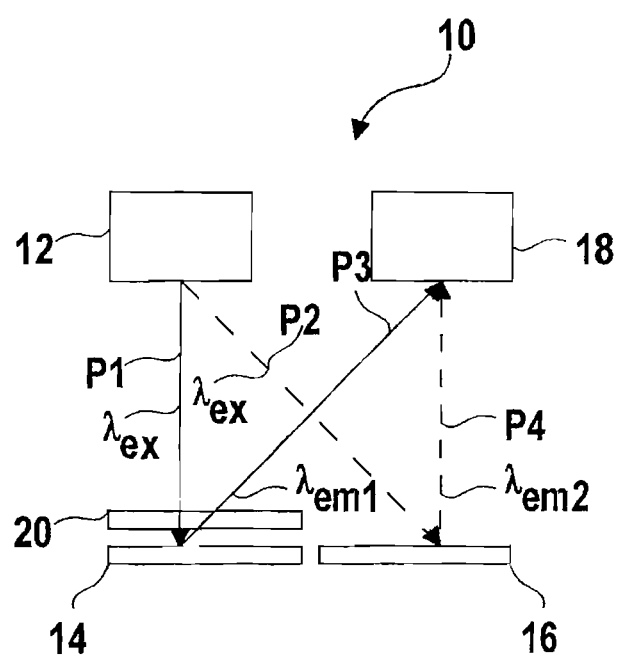
FIG. 1 shows a schematic illustration of a device for analyzing a sample containing fluorophores according to a first embodiment of the invention.

FIG. 1 shows a schematic illustration of a device 10 for analyzing a sample 16 containing fluorophores according to a first embodiment of the invention. The device 10 comprises a light source 12 which emits light having a wavelength $\lambda_{ex}$ onto an internal reference standard 14 which serves as a reference object and onto the sample 16 supplied to the device 10 in the form of a test strip, as schematically illustrated by the arrows P1 and P2. The light emitted from the internal reference standard 14 has a wavelength $\lambda_{em1}$ and, as indicated by the arrow P3, is incident on a detection area of a detector 18. The light emitted from the sample 16 and having a wavelength $\lambda_{em2}$ is incident on the detection area of the detector 18, as indicated by the arrow P4. The light source 12 sequentially emits light onto the reference standard 14 and the sample 16. A filter 20 arranged between the light source 12 and the internal reference standard 14 causes that the different spectral curves of the excitation efficiency of the internal reference standard 14 and of the spectral sensitivity of the fluorophores of the sample 16 given a change in the wavelength $\lambda_{ex}$ of the light emitted from the light source 12 adapt to each other. As a result thereof, in the case of a change in wavelength of the light radiation generated by the light source 12, the analysis result of the device 10 is not or only slightly influenced. In the embodiment of the invention, the reference standard 14 contains fluorophores and is also referred to as fluorescence standard.

Figure 2:
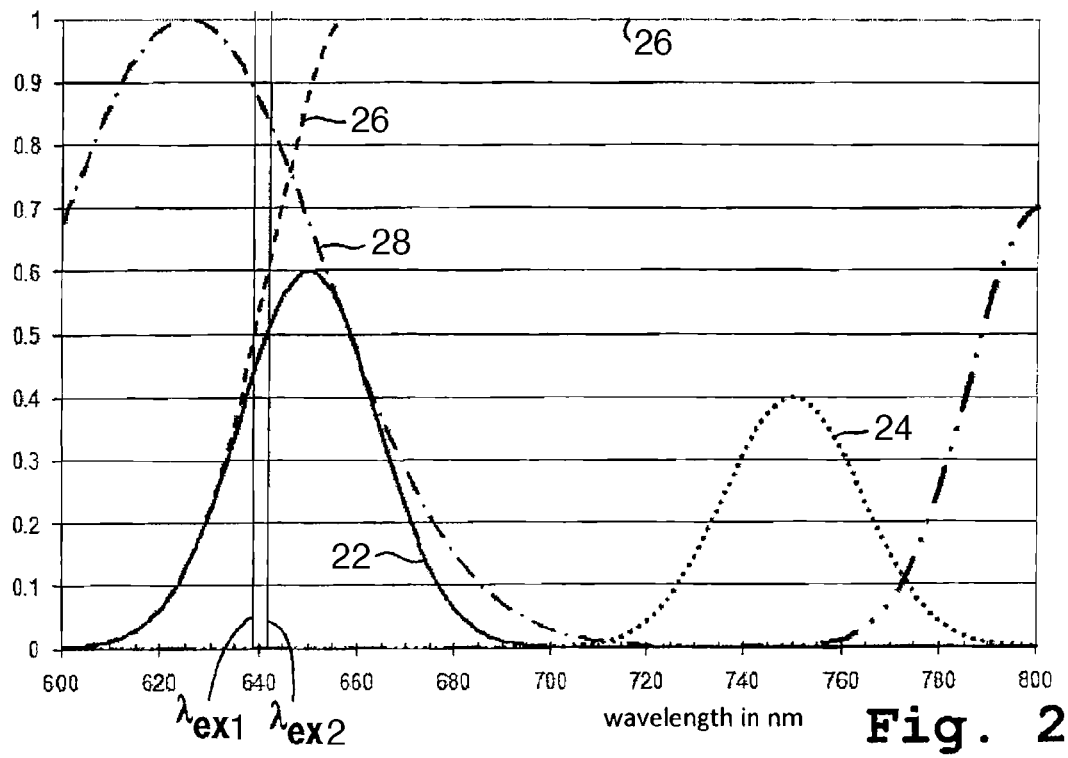
FIG. 2 shows a diagram with the curves of the transmission properties of the filter, the excitation efficiency of the reference object, the excitation efficiency of the fluorophore and the emission spectrum of the fluorophore as a function of the wavelength in the first embodiment of the invention.
Figure 3:
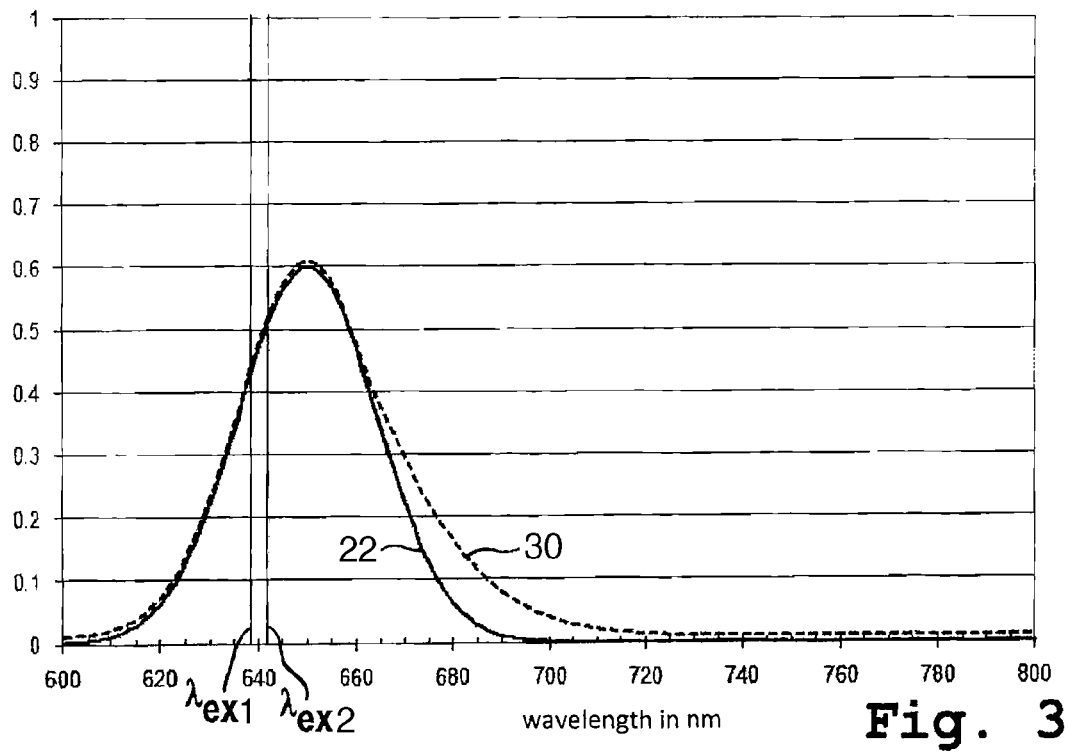
FIG. 3 shows a diagram with the curves of the excitation efficiency of the fluorophore and the resulting excitation efficiency of the reference object changed by the filter in the first embodiment of the invention.

In FIG. 2, a diagram with the spectral curves of the excitation efficiency 22 of the fluorophore, of the emission spectrum 24 of the fluorophore, of the transmission characteristic 26 of the filter 20 and of the excitation efficiency 28 of the internal reference standard 14 is illustrated. Here, the wavelength $\lambda_{ex1}$ is the nominal wavelength of the light source 12, which in the present embodiment is 638 nm, and the wavelength $\lambda_{ex1}$ is the change in wavelength of the light source 12 caused due to the aging of components of the light source 12 and/or due to environmental influences, such as a change in temperature. In the present embodiment, the wavelength $\lambda_{ex2}$ is, for example, 642 nm. When the wavelength of the light emitted from the light source 12 changes from 638 nm to 642 nm, the excitation efficiency of the fluorophore contained in the sample 16 increases from the factor 0.44 to the factor 0.51 and thus from 44% to 51%. However, given a change in the wavelength $\lambda_{ex}$ from 638 nm to 642 nm, the excitation efficiency 28 of the reference object decreases from 0.89 to 0.85 and thus from 89% to 85%. In the case of a quantitative determination of the fluorophores in the sample 16 on the basis of a comparison of the measurement value detected by the detector 18 when the sample 16 is irradiated and the measurement value detected by the detector 18 when the internal reference standard 14 is irradiated, this results in a considerable evaluation error in the evaluation of the measurement values. In the present embodiment, the filter 20 causes, at least in the range between the wavelength $\lambda_{ex1}$ and $\lambda_{ex2}$, a coincidence of the resulting excitation efficiency of the internal reference standard 14 caused by the filter 20. The spectral curve of the resulting excitation efficiency of the internal reference standard 14 caused by the filter 20 is shown in FIG. 3 by the curve 30. The curve 30 results from the product of the excitation efficiency 28 and the transmission characteristic 26 of the filter 20, as shown in FIG. 2.

As shown in FIG. 3, the excitation efficiency 22 of the fluorophores of the sample and the curve 30 of the resulting excitation efficiency of the internal reference standard 14 change in the range between the first wavelength $\lambda_{ex1}$ and the second wavelength $\lambda_{ex2}$ in the same manner so that as a result thereof, given a change in wavelength in this range between $\lambda_{ex1}$ and $\lambda_{ex2}$ the resulting excitation efficiency 30 as well as the excitation efficiency 22 are changed in the same manner so that given a relative determination of the quantity of the fluorophores in the sample 16 this sample 16 is directly evaluated and measurement errors of the device 10 can be avoided or, respectively, compensated for by the filter 20.

Figure 4:
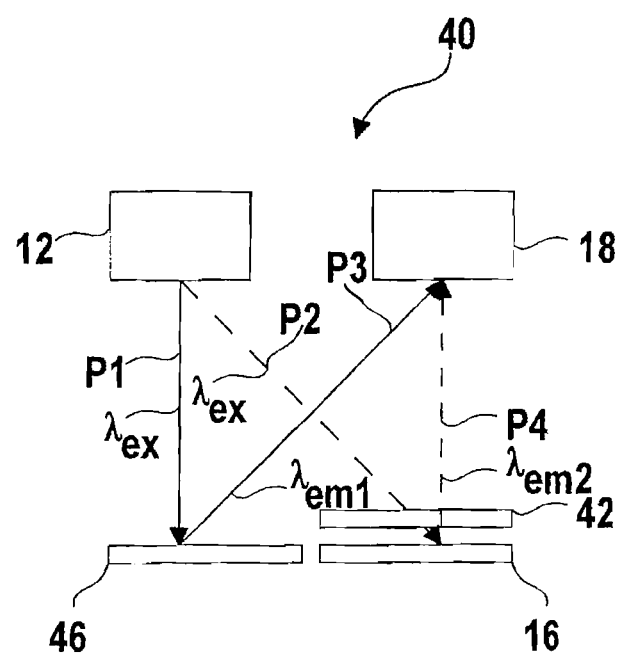
FIG. 4 shows a schematic illustration of a device for analyzing a sample containing fluorophores according to a second embodiment of the invention.

In FIG. 4, a schematic illustration of a device 40 for analyzing the sample 16 containing fluorophores according to a second embodiment of the invention is shown. Elements having the same structure or the same function are identified with the same reference signs.

Figure 5:
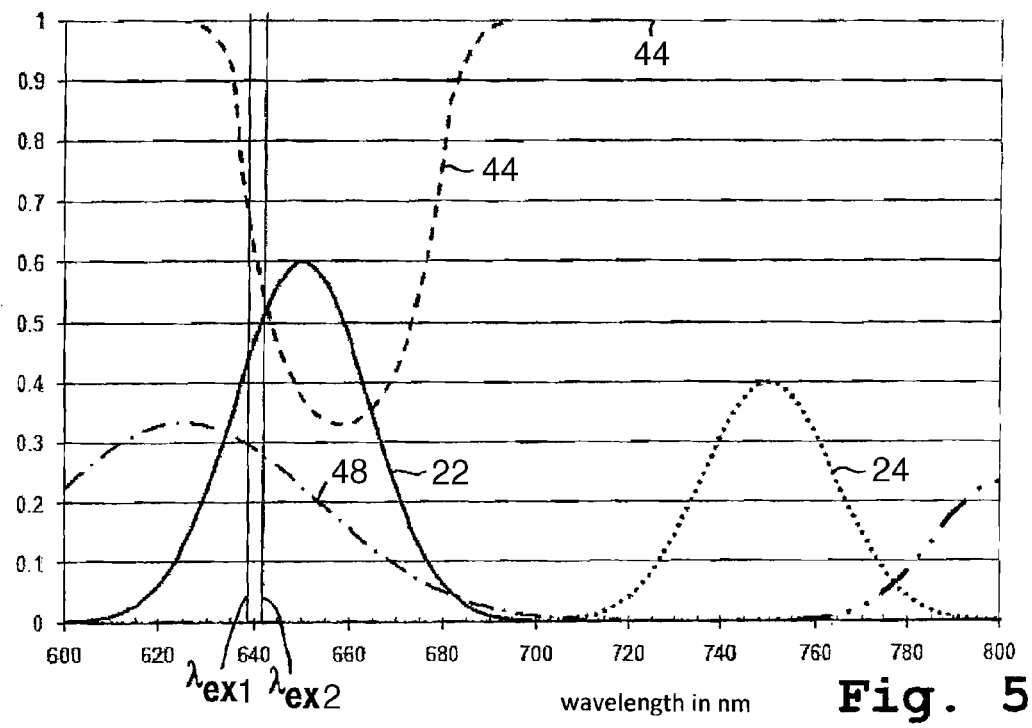
FIG. 5 shows a diagram with the curves of the transmission properties of the filter, the excitation efficiency of the reference object, the excitation efficiency of the fluorophore and the emission spectrum of the fluorophore as a function of the wavelength in the second embodiment of the invention.
Figure 6:
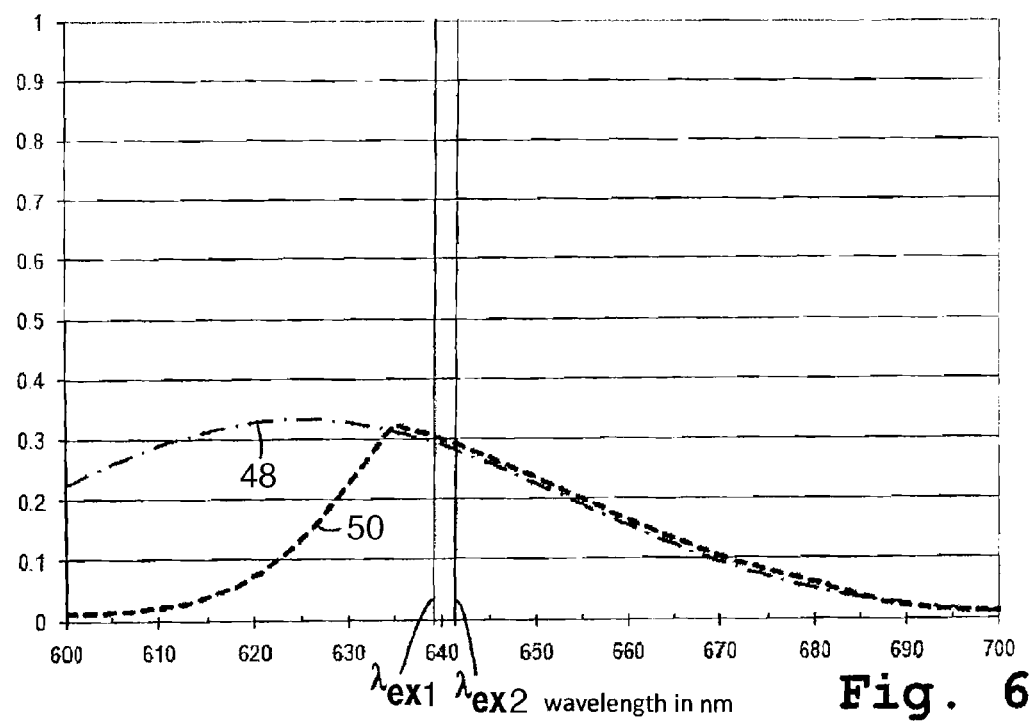
FIG. 6 shows a diagram with the curves of the excitation efficiency of the fluorophore and the resulting excitation efficiency of the reference object changed by the filter in the second embodiment of the invention.

In contrast to the first embodiment according to FIG. 1, instead of the filter 20 arranged between the light source 12 and the internal reference standard 14, in the second embodiment of the invention a filter 42 is provided that is arranged between the light source 12 and the sample 16. The spectral curve of the transmission characteristic of the filter 42 is illustrated in FIG. 5 and identified with the reference sign 44. Further, the internal reference standard 46 used in the second embodiment has an excitation efficiency deviating from the internal reference standard 14, and whose curve is identified with the reference sign 48 in FIG. 5. However, the reference standard 46, too, contains fluorophores. By the filter 42, the spectral curve of the resulting excitation efficiency is changed as a result of the combination of the filter 42 and the sample 16 and it extends in the relevant wavelength range between the wavelength $\lambda_{ex1}$ and $\lambda_{ex2}$ parallel to the excitation efficiency 48 of the reference standard 46, as shown by the curve 50 in FIG. 6.

Figure 7:
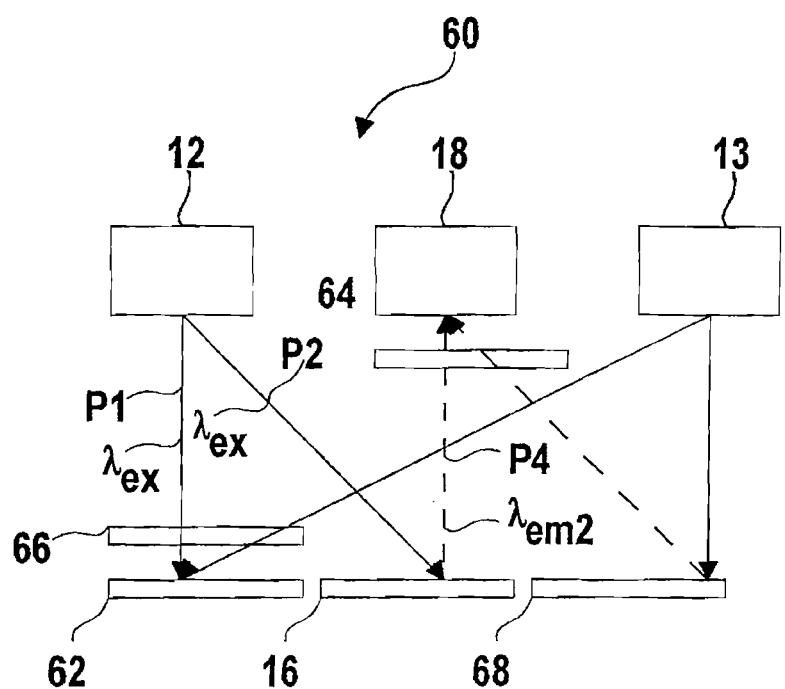
FIG. 7 shows a schematic illustration of a device for analyzing a sample containing fluorophores according to a third embodiment of the invention.
Figure 8:
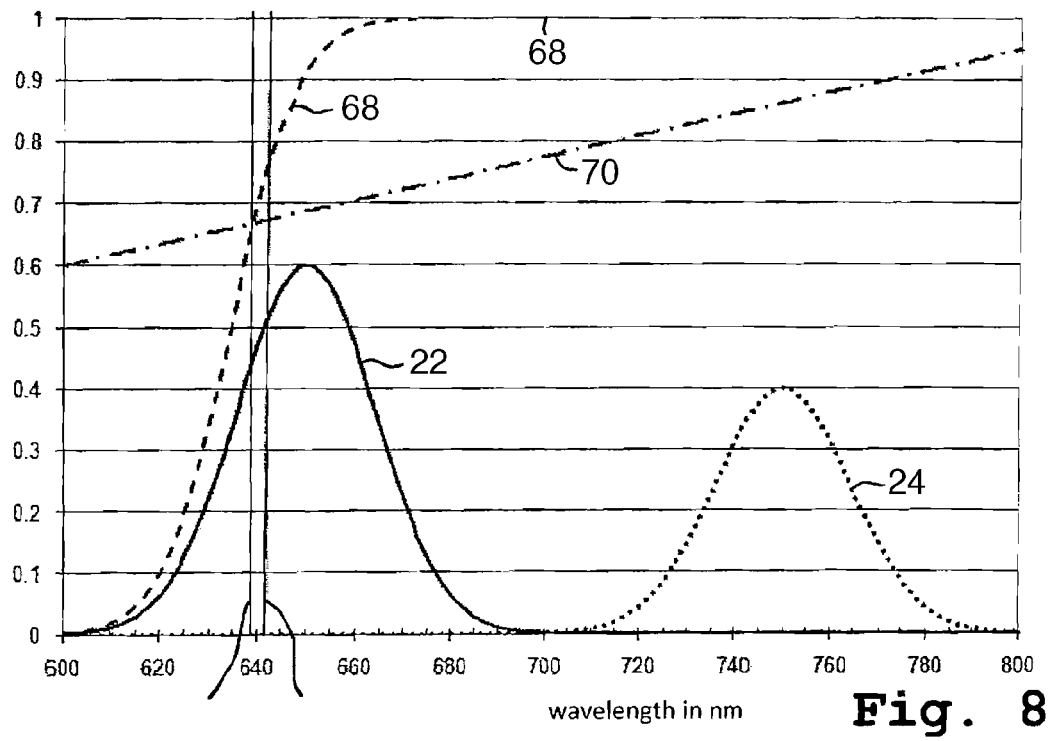
FIG. 8 shows a diagram with the curves of the transmission properties of the filter, the excitation efficiency of the reference object, the excitation efficiency of the fluorophore and the emission spectrum of the fluorophore as a function of the wavelength in a third embodiment of the invention.
Figure 9:
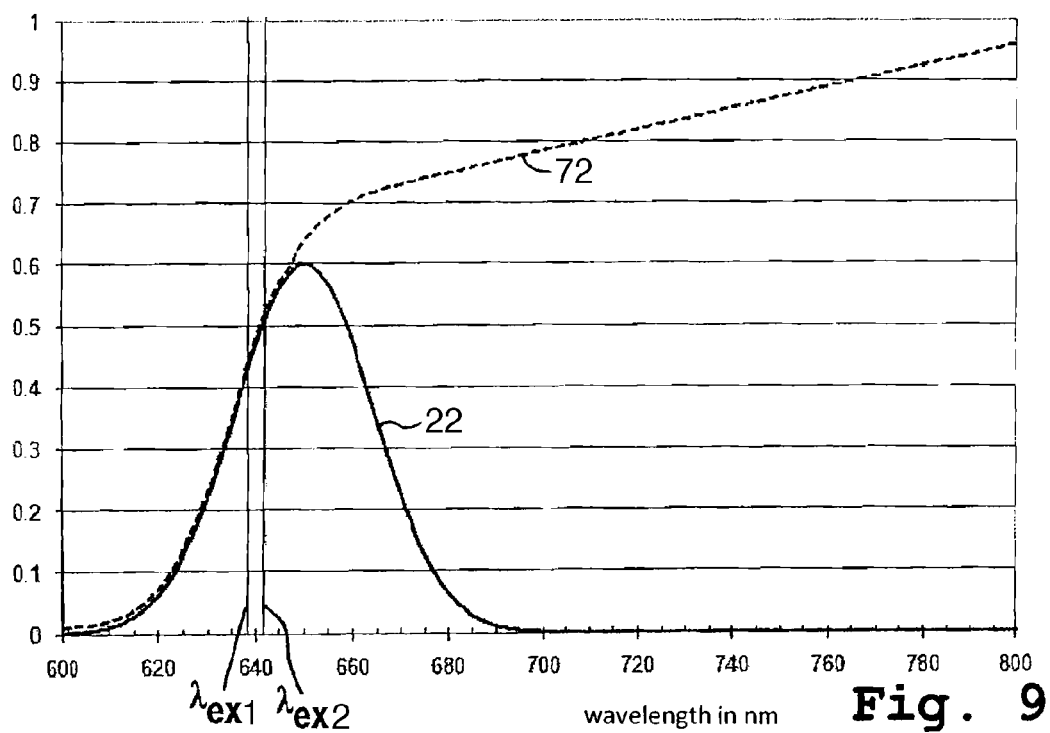
FIG. 9 shows a diagram with the curves of the excitation efficiency of the fluorophore and the resulting excitation efficiency of the reference object changed by the filter in the third embodiment of the invention.

In FIG. 7, a schematic illustration of a device 60 for analyzing a sample 16 containing fluorophores according to a third embodiment of the invention is shown. The device 60 comprises a monitor diode 62. The light source 12 serves as an excitation light source and emits excitation light both onto a monitor diode 62 for monitoring the intensity of the light radiation generated by the light source 12 and onto the sample 16. The light emitted from the sample 16 is incident on the detector element 18, wherein a filter 64 is arranged between the sample 16 and the detector element 18 to filter out the light of the light source 12 that is reflected on the sample 16 and to only supply the fluorescence light emitted from the fluorophores contained in the sample 16 to the detection area of the detector 18. Likewise, in the embodiments according to FIG. 1 and according to FIG. 4, a filter can be provided in the path P4 for filtering out the excitation light emitted from the light source 12 and reflected by the sample 16. The device 60 comprises a second inventive filter 66 which is arranged between the light source 12 and the monitor diode 62 and whose transmission characteristic is illustrated in FIG. 8 by the curve 68. The detection sensitivity of the monitor diode 66 is illustrated in FIG. 8 by the curve 70. By the combination of the transmission characteristic 68 of the filter 66 and the detection characteristic 70 of the monitor diode 62 the resulting transmission characteristic 72 of the combination of filter 66 and monitor diode 62 as illustrated in FIG. 9 results. In the range between the wavelengths $\lambda_{ex1}$ and $\lambda_{ex2}$, the curves of the resulting detection sensitivity 72 and the excitation efficiency 22 coincide so that as a result thereof, effects of a change in wavelength of the excitation light of the excitation light source 12 from $\lambda_{ex1}$ to $\lambda_{ex2}$ or, respectively, of a wavelength in the range between $\lambda_{ex1}$ and $\lambda_{ex2}$ has no such effect that the change in wavelength distorts the measurement result of the device 60.

The device 60 further comprises a reference light source 13 which emits light of a reference light wavelength onto the reference standard 68 and the monitor diode 62. The excitation light source 12 and the reference light source 13 are operated alternatively, so that the light emitted due to the reference light from the reference standard 68, i.e. fluorescence light and/or reflected light, is detected by the detector unit 18, the light emitted from the reference light source 13 being simultaneously detected by the monitor diode 62. In the present embodiment, the reference light is passed through the filter 66, wherein in the wavelength range of the reference light emitted from the reference light source 13 the filter 66 has a substantially lower influence on the reference light than in the wavelength range of the excitation light of the excitation light source 12. Preferably, the reference light of the reference light source 13 has a wavelength which lies in the wavelength spectrum of the fluorescence light emitted from the sample 16 and does not lie in the wavelength range of the excitation light.

Figure 10:
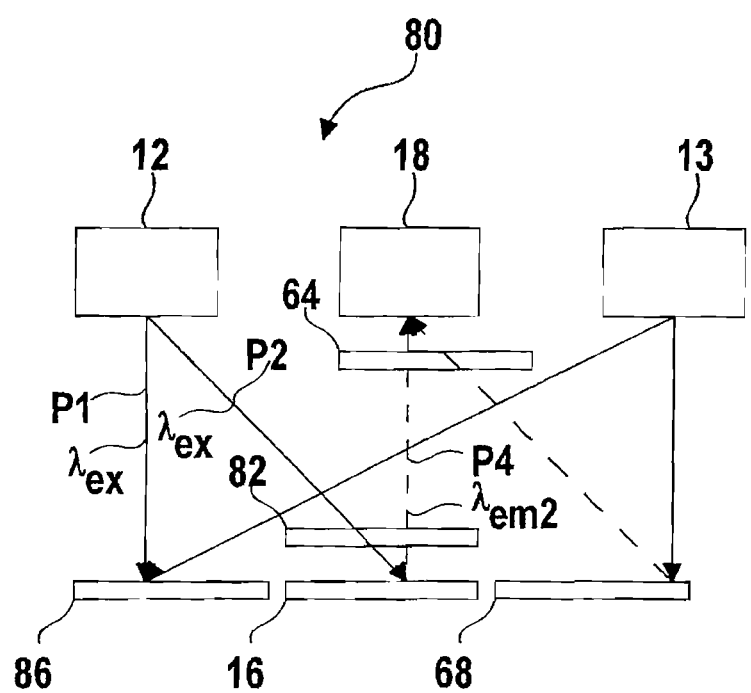
FIG. 10 shows a schematic illustration of a device for analyzing a sample containing fluorophores according to a fourth embodiment of the invention.

In FIG. 10, a schematic illustration of a device 80 for analyzing a sample 16 containing fluorophores according to a fourth embodiment of the invention is illustrated.

Figure 11:
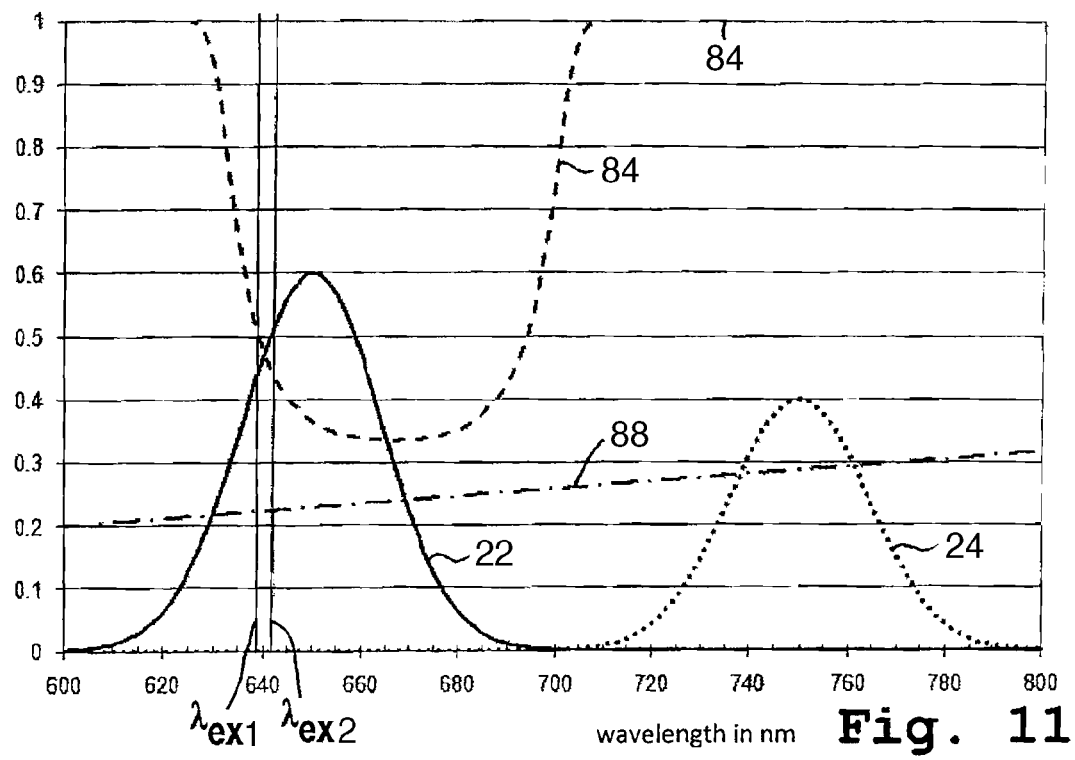
FIG. 11 shows a diagram with the curves of the transmission properties of the filter, the excitation efficiency of the reference object, the excitation efficiency of the fluorophore and the radiation spectrum of the fluorophore as a function of the wavelength in the fourth embodiment of the invention.
Figure 12:
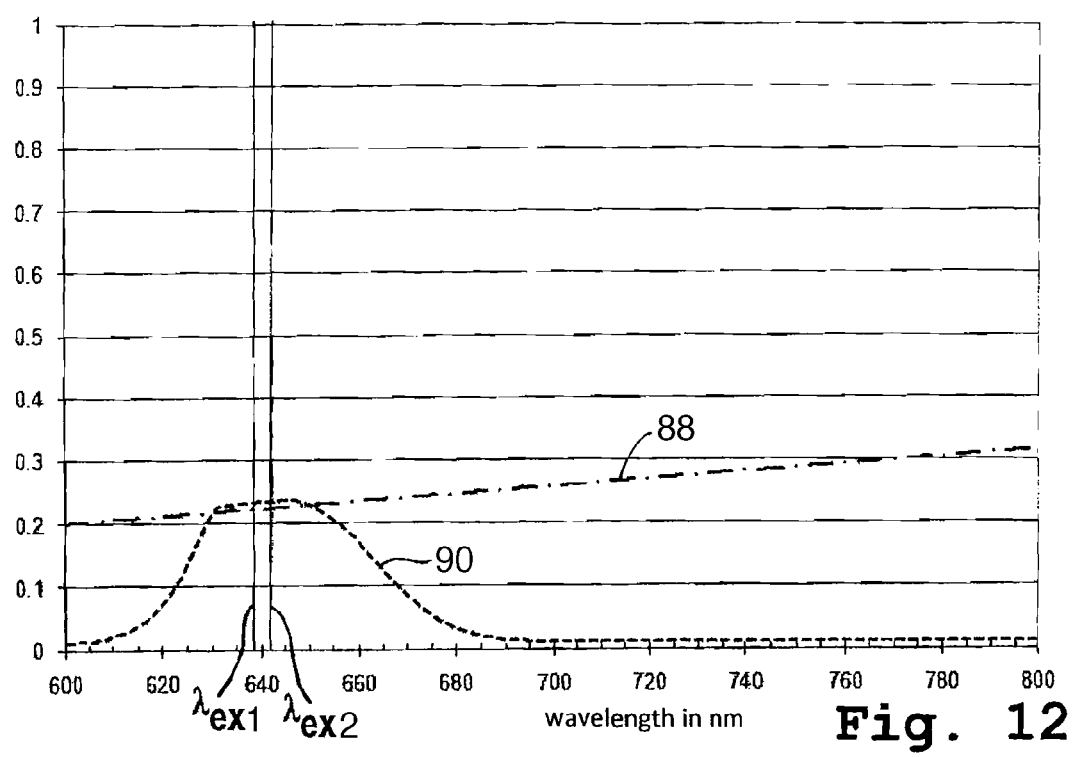
FIG. 12 shows a diagram with the curves of the excitation efficiency of the fluorophore and the resulting excitation efficiency of the reference object changed by the filter in the fourth embodiment of the invention.

In contrast to the device 60 according to FIG. 7, instead of the filter 66 between the excitation light source 12 and the monitor diode 62 (FIG. 7) a filter 82 is arranged between the light source 12 and the sample 16. The curve of the transmission characteristic of the filter 82 is identified with the reference sign 84 in FIG. 11. The detection sensitivity of the monitor diode 86 is lower than the detection sensitivity of the monitor diode 62 according to FIG. 7 and is illustrated in FIG. 11 by the curve 88. By the filter characteristic 84 of the filter 82, there results the resulting excitation efficiency 90 illustrated in FIG. 12, which results from the combination of the curve of the excitation efficiency 22 of the fluorophores of the sample 16 and the filter characteristic 84 of the filter 82. In the range between the wavelength $\lambda_{ex1}$ and $\lambda_{ex2}$, then the resulting excitation efficiency 90 extends parallel to the spectral detection sensitivity 88 of the monitor diode 86 so that as a result thereof measurement errors due to the change in wavelength of the light source in the range between the wavelengths $\lambda_{ex1}$ and $\lambda_{ex2}$ can be reduced or completely removed.

Figure 13:
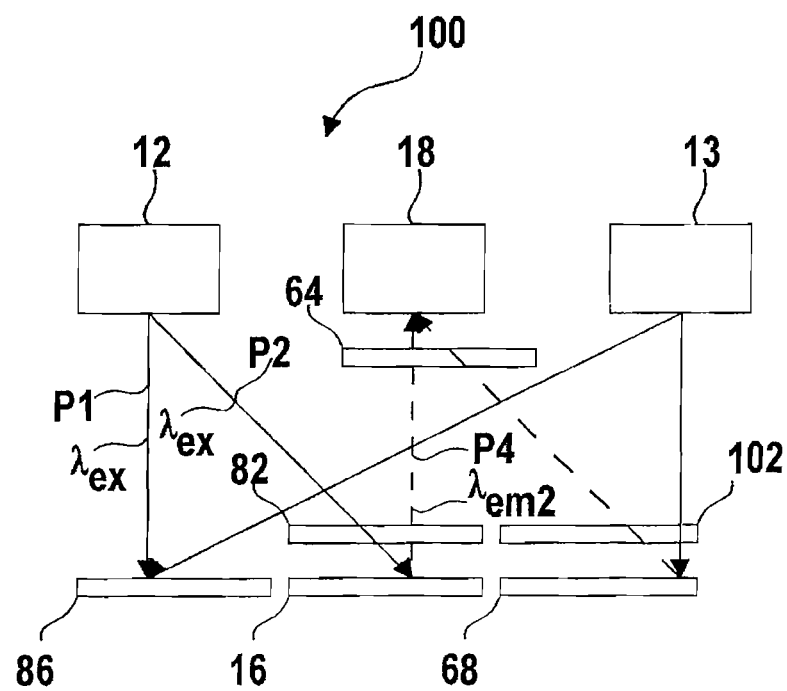
FIG. 13 shows a schematic illustration of a device for analyzing a sample containing fluorophores according to a fifth embodiment of the invention.

In FIG. 13, a schematic illustration of a device 100 for analyzing a sample 16 containing fluorophores according to a fifth embodiment of the invention is shown. In contrast to the device 80 according to FIG. 10, a further filter 102 is provided between the reference light source 13 and the reference standard 68. By means of the filter 102, the spectral characteristic of the reference standard 68 can be adapted to the spectral curve of the detection sensitivity of the monitor diode 86.

Likewise, the filter 66 in the third embodiment of the invention according to FIG. 7 can have such a fourth characteristic that it adapts both the spectral detection sensitivity of the monitor diode 62 to the spectral curve of the excitation efficiency of the fluorophores of the sample 16 and to the excitation efficiency or, respectively, the emission efficiency of the reference element 68. The reference element 68 is also referred to as reference object, serves as a reference standard and can be designed as an optical element.

Further, the filter 66 and the monitor diode 62 can be arranged within one unit, in particular the filter 66 can be designed as a coating of a surface of the detection area of the monitor diode 62. Also, the reference standard 68 can be combined in an arrangement with the filter 102, in particular the filter 102 can be applied as a coating on the reference standard 68.

In particular, the ratio of the energy supplied to the reference object via the immitted light to the energy emitted from the reference object is regarded as emission efficiency. Here, the energy which is emitted from the reference object and is relevant for the emission efficiency can be caused by a reflection of a part of the irradiated light, by a transmission of the emitted light or by an excitation of a substance contained in the reference object for emitting a radiation. Such a substance can in particular comprise a suitable fluorophore.

In all embodiments of the invention, the spectral curves of reference standard and fluorophore as well as between monitor diode and sample are adapted to each other in the relevant wavelength range so that the effect on a measurement result due to the changes in wavelength can be minimized or completely compensated for. Embodiments of the invention are also possible in which the device has both a reference object and a sample as well as a monitor diode, wherein then the detection sensitivity of the monitor diode, the excitation efficiency of the fluorophore and the excitation efficiency of the reference object are adapted to each other and have a parallel curve at least in a relevant wavelength range in which variations of the wavelength of the light emitted from the light source 12 might occur. Instead of a filter between the light source and the reference object or between the light source and the sample 16, each time a filter can be arranged between the light source and the reference element and the light source and the sample to adapt the curves of the excitation efficiencies of the fluorophores of the sample and of the fluorophores of the reference object to each other. Further, both a first filter between the light source and the monitor diode and a second filter between the light source and the sample can be provided to adapt the detection sensitivity of the monitor diode and the excitation efficiency of the sample in the relevant spectral range between $\lambda_{ex1}$ and $\lambda_{ex2}$.

The invention claimed is:

1. A device for determining the concentration of fluorophores in a sample,
    with a reference light source for emitting reference light onto an optical reference object and for emitting reference light onto a monitor diode, wherein the optical reference object couples in a part of the reference light emitted from the reference light source in the direction of a detection element,
    with an excitation light source for emitting excitation light onto the fluorophores of the sample and for emitting excitation light onto the monitor diode, wherein the fluorophores of the sample emit fluorescence light in the direction of the detection element given an immission of excitation light,
    wherein the fluorophores, given immission of excitation light of a first wavelength, have a first excitation efficiency and, given an immission of excitation light of a second wavelength, have a second excitation efficiency,
    wherein the monitor diode, given an immission of excitation light of a first wavelength, has a first detection sensitivity and, given an immission of excitation light of a second wavelength onto the monitor diode, has a second detection sensitivity,
    with an optical element which is arranged between the excitation light source and the sample and/or between the excitation light source and the monitor diode and/or as an optically effective layer on the monitor diode and which, due to its optical property, adapts a first difference between the first excitation efficiency and the second excitation efficiency and a second difference between the first detection sensitivity and the second detection sensitivity to each other.

2. The device according to claim 1, characterized in that the first wavelength is the nominal wavelength of the excitation light source and in that the second wavelength is a wavelength different from the first wavelength, which in particular results due to temperature influences and/or aging of at least one component of the excitation light source.

3. The device according to claim 2, characterized in that the optical element adapts the spectral curve of the excitation efficiency of the sample and the spectral curve of the detection sensitivity of the monitor diode at least in the wavelength range between the first wavelength and the second wavelength.

4. The device according to claim 2, characterized in that the difference between the first wavelength and the second wavelength is in the range between 0.1 nm to 5 nm.

5. The device according to claim 1, characterized in that the device has a detection element for detecting the light emitted from the sample given an immission of light of the light source onto the sample and/or for detecting the light emitted from the reference object given an emission of light of the light source onto the reference object.

6. The device according to claim 1, characterized in that the optical property of the optical element influences the light emitted from the sample given the immission of light of the light source and/or the light emitted from the reference object such that the first difference is approximated to the second difference, preferably that the second difference is equal to the first difference.

7. The device according to claim 1, characterized in that the optical element adapts the spectral curve of the excitation efficiency of the sample and the spectral curve of the detection sensitivity of the monitor diode at least in the wavelength range between the first wavelength and the second wavelength.

8. The device according to claim 1, characterized in that the optical element is a filter and in that the optical property of the optical element is the transmission property of the filter.

9. The device according to claim 1, characterized in that the light source, the excitation light source and/or the reference light source comprise a
    laser light source, an LED light source or a white light source with a filter arrangement for generating light in a narrow-band range, wherein the first wavelength lies within the narrow-band range, preferably in the middle thereof.

10. The device according to claim 1, characterized in that a control unit sequentially activates the excitation light source and the reference light source.

11. The device according to claim 1, characterized in that the reference object serves as an internal reference standard, as a calibration standard and/or as a quality assurance standard.

12. The device according to claim 1, characterized in that the reference object comprises a fluorescence standard and/or an optical element serving as a reference standard.

* * * * *